United States Patent [19]

Ellinger et al.

[11] Patent Number: 4,815,323
[45] Date of Patent: Mar. 28, 1989

[54] ULTRASONIC FUEL QUANTITY GAUGING SYSTEM

[75] Inventors: S. Michael Ellinger, North Ferrisburg, Vt.; Howard P. Jones, Salt Lake City, Utah

[73] Assignees: Simmonds Precision Products, Inc., Tarrytown, N.Y.; Edo Corporation, Salt Lake City, Utah

[21] Appl. No.: 4,750

[22] Filed: Jan. 9, 1987

Related U.S. Application Data

[63] Continuation-in-part of Ser. No. 750,817, Jun. 28, 1985, abandoned.

[51] Int. Cl.[4] .................. G01F 23/28; G01N 9/00; G01N 25/00
[52] U.S. Cl. .................. 73/290 V; 73/32 A; 73/292; 364/509; 374/142
[58] Field of Search .................. 73/290 V, 291, 292, 73/32 A; 374/142; 364/509

[56] References Cited

U.S. PATENT DOCUMENTS

| | | | |
|---|---|---|---|
| 3,290,944 | 12/1966 | Altman et al. | 73/290 V X |
| 3,834,233 | 9/1974 | Willis et al. | 73/290 V |
| 4,118,983 | 10/1978 | Brazhnikov | 340/621 X |
| 4,403,502 | 9/1983 | Lindt | 73/290 V X |
| 4,420,976 | 12/1983 | Orloff et al. | 73/304 C |
| 4,442,700 | 4/1984 | Swoboda | 73/32 A |
| 4,451,894 | 5/1984 | Dougherty et al. | 73/304 C X |
| 4,531,406 | 7/1985 | Fritz | 73/290 V |
| 4,580,448 | 4/1986 | Skrgatic | 367/908 X |
| 4,700,569 | 10/1987 | Michalski et al. | 364/509 X |

FOREIGN PATENT DOCUMENTS 2152667 8/1985 United Kingdom ............ 73/290 V Primary Examiner—Daniel M. Yasich
Attorney, Agent, or Firm—Dale R. Lovercheck

[57] ABSTRACT

A method of measuring aircraft fuel quantity and density in a fuel container using an ultrasonic transducer; a stillwell liquid fuel; a computer control, an indicator and an altitude sensor. The computer control includes a central processing unit connected to each of the ultrasonic transducers. The altitude sensor is connected to the central processing unit. The indicator means is connected to the central processing unit. The stillwell is supported by the container. Each ultrasonic transducer is supported within the stillwell by the container. The liquid fuel is supported within the container. An ultrasonic signal is transmitted from the transducer within the stillwell. The reflected ulrasonic signal is received by the transducer within the stillwell. The round-trip time period from sending to reciving the signal is measured. The quantity of fuel in the container is determined from the round-trip time period and stored data on the container volume in the central processing unit.

2 Claims, 3 Drawing Sheets

ULTRASONIC FUEL QUANTITY GAUGING SYSTEM

This invention relates to Aircraft Fuel Quantity Gauging System (FQGS) New Technology Investigation Ultrasonic System Study Program, July 1984, prepared for Naval Air Development, Warminster, Pa. 18974, Contract N62269-83-R-0252, prepared by S. M. Ellinger and R. Michaud, the content and disclosure of which is incorporated herein by reference in its entirety.

Ewen, in U.S. Pat. No. 4,116,239 discloses an ultrasonic oxygenation instrument having an ultrasonic transducer having a nozzle attached thereto.

This application is a continuation-in-part of Ser. No. 06/750,817, filed June 28, 1985, and now abandoned.

BRIEF SUMMARY OF THE INVENTION

Figure 1:
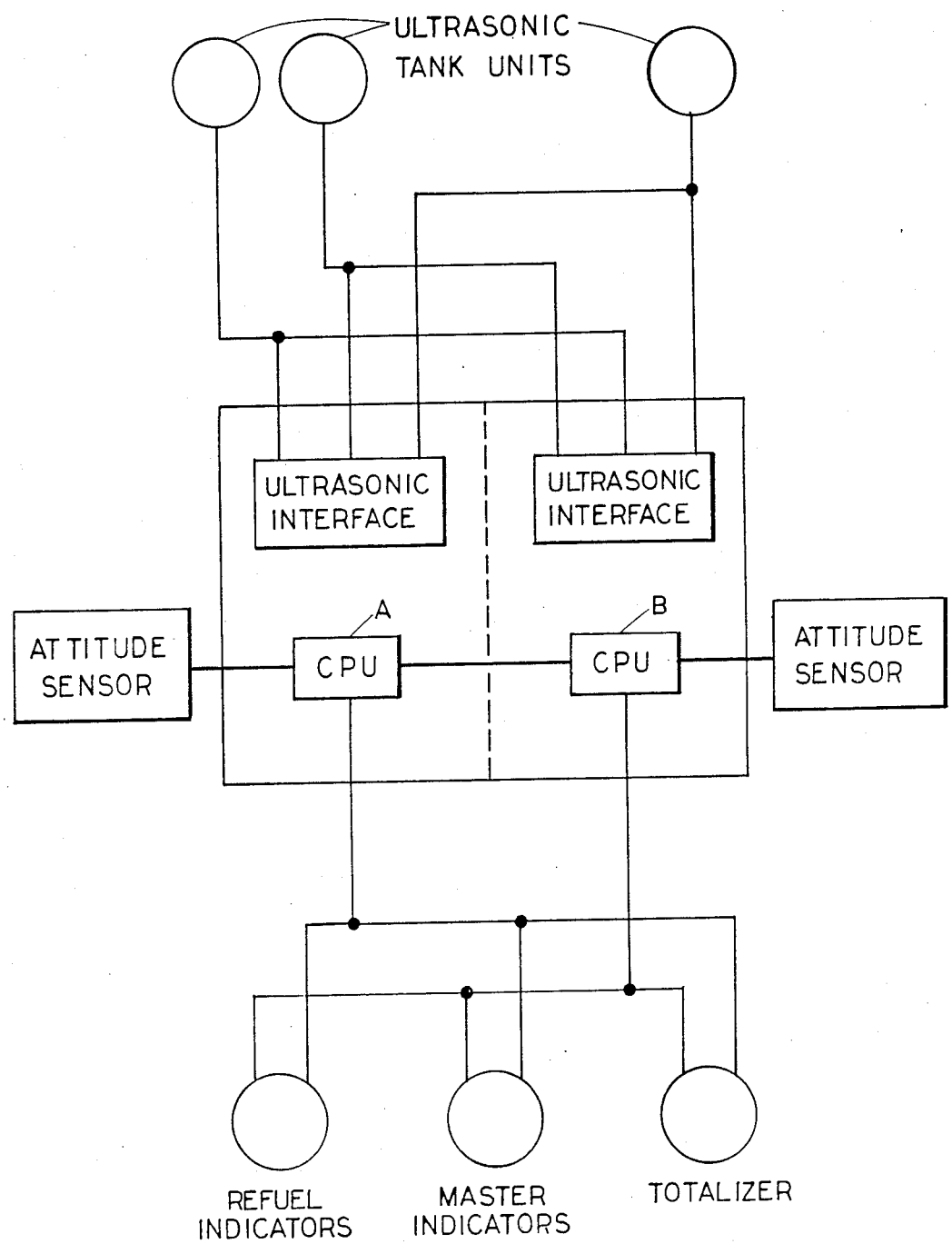
FIG. 1 is a schematic presentation of an ultrasonic fuel quantity gauging system in accordance with the invention.

A method of measuring aircraft fuel quantity and density including (a) providing a fuel container means, an ultrasonic transducer, a temperature sensor means, a stillwell, liquid fuel, a computer control means, indicator means and the computer control means comprising a central processing unit and memory means, the memory having container volume and fuel temperature data stored therein; the central processing unit being connected to each ultrasonic sensor means and to the temperature sensor means, the indicator means being connected to the central processing unit; the stillwell being supported by the container means; the ultrasonic transducer being supported with the stillwell by the container means; the liquid fuel being supported within the container means; (b) transmitting an ultrasonic signal from the transducer within the stillwell; (c) receiving the ultrasonic signal by the transducer within the stillwell; (d) measuring the round-trip time period from the transmitting to the receiving the signal; (e) determining the quantity of fuel in the container from the round-trip period and the stored data on the container volume in the central processing unit; (f) determining the density of the fuel from the stored temperature data.

DETAILED DESCRIPTION OF THE INVENTION

A revolutionary new fuel quantity gauging system (FQGS) for aircraft based on ultrasonics is described which inherently eliminates the problems associated with the existing capacitance measuring system. The existing capacitance system was designed to meet Class I accuracy requirements of ±6% with degradation of the original fiberglass probes, analog circuit drift, deterioration of the coax wiring, and water on the compensator. The accuracy can reach levels which essentially make the system useless and certainly not credible to the crew.

The ultrasonic concept is similar to a sonar system and measures the round-trip time of an acoustic pulse from the bottom of the tank to the fuel surface and back. This is a timing measurement which utilizes digital measuring techniques and is thus not affected by the parameters that plague the existing analog system.

Advantages of the ultrasonic fuel quantity measurement of the invention include: system accuracy is based on digital timing measurements rather than analog amplitude measurements. This eliminates the need for calibration, and provides for a stable output that is not affected by component variations due to temperature, aging and voltage changes. Performance is not degraded due to water and fuel contaminations. The electrical wiring and sensor can be mounted outside the tank making it intrinsically safe for any transient or accident that may happen to the wiring. Inferred density based on speed of sound and temperature is more accurate than dielectric constant. Fuel stratification is measured directly from the top to the bottom of the tank. Mass is thus more accurately determined based on average density.

The ultrasonic system is digital and requires no calibration. The ultrasonic system does not drift and is not affected by component changes like an analog system.

Crew confidence is high because of agreement between repeater and master indicators through the utilization of digital measuring techniques which are far more accurate and repeatable than analog approaches.

Performance comparison between the existing capacitance and proposed ultrasonic FQGS is given in Table I.

TABLE I

| Prior Capacitance FQG System | Ultrasonic FQG System of the Invention |
| --- | --- |
| Analog System | Digital System |
| Degrades due to Coax Wire Aging Drifts | Insensitive to Wiring No Drift |
| Requires Calibration | No Calibration |
| Affected by Water and Fuel Contaminants | Insensitive to Water and Fuel Contaminants |
| Density Inferred by Dielectric Constant - Worst Case 3%, Typically 1.5% | Direct Density Measurement - Worst Case 0.5% for any Fuel Type or Mixture |
| Max Error Due to Attitude 2.5% | Attitude Sensor of Pitch and Roll to within 1° Max Error 0.3% due to Attitude |
| System Error 7.5% Full Scale No Fault Isolation | System Error 0.7% Fault Isolation to the Sensor and Card Level |
| System MTBF 117 Hours No Redundancy. Failure or Degradation of a Flight Station Indicator Affects Total Indicator and Refuelling Indicator as Well | System MTBF 3987 Hours System Redundancy with Exception to Sensors |

PREFERRED EMBODIMENT OF A SYSTEM OF THE INVENTION

The block diagram for a preferred ultrasonic system is shown in FIG. 1. Ultrasonic tank units are connected to indicator through redundant ultrasonic interfaces, central processing units (CPU) A and B. The sensors located in the aircraft fuel tanks are multiplexed by two redundant synchronized processors. With exception to the sensors, the system is completely redundant. Failure of a sensor interface of one processor will not affect input to the other processor. Separate reference and density measurements are made in each tank. Aircraft attitude sensors measure pitch and roll to within ±0.5°.

The processor performs height-volume calculations, corrects for attitude, converts volume to mass, performs built-in test and validity checks, and outputs data to the indicators.

Identical indicators with a numeric and sunburst display provide a digital as well as an analog display of fuel quantity for the master, refuel, and totalizer indicators. Each processor provides separate inputs to each indicator which in turn selects the quantity to be displayed. The indicator also has a separate numeric error code display which isolates a problem to the SRA level.

The fuel mass is calculated using ultrasonic reflection times from the fuel surface, velocity reference reflector, and the mobile density reference. The calculation also uses height-volume tables, specific to each probe position, and attitude correction tables.

Provided that the velocimeter is below the fuel surface, the raw velocimeter echo time is averaged over eight (8) readings to provide a smoothed value.

The input fuel surface and density reference reflection echo is digitally filtered using an infinite impulse response filter to minimize surface ripple and related effects.

The fuel height is calculated using the velocimeter time, known reference distance, and fuel surface reflection time.

$$\text{Fuel Height} = \frac{\text{Fuel Surface Time}}{\text{Velocimeter Time}} \times \text{Velocimeter Distance}$$

The fuel volume is determined by use of height-volume tables stored in the Computer Control Unit (CCU) memory for each probe position. The tables have values for one-inch increments at the required calibration attutude.

First the fuel volume is linearly interpolated between the one-inch increments to the calculated fuel height.

Then the fuel volume is calculated by linear interpolation of the fuel volume and attitude correction factors.

The density of the fuel is determined calculating the density reference position (bottom of float) relative to the fuel surface and using this value to look up the density in a table stored in the CCU program memory.

First the density reference position is calculated using the velocimeter echo time and known reference position. Then the difference between fuel height and reference height are used to determine the density from the look-up table. Relative Reference Position=Fuel Height−Reference Height.

The fuel mass is calculated as the product of density and volume. Fuel Mass=Fuel Density×Fuel Volume.

Figure 2:
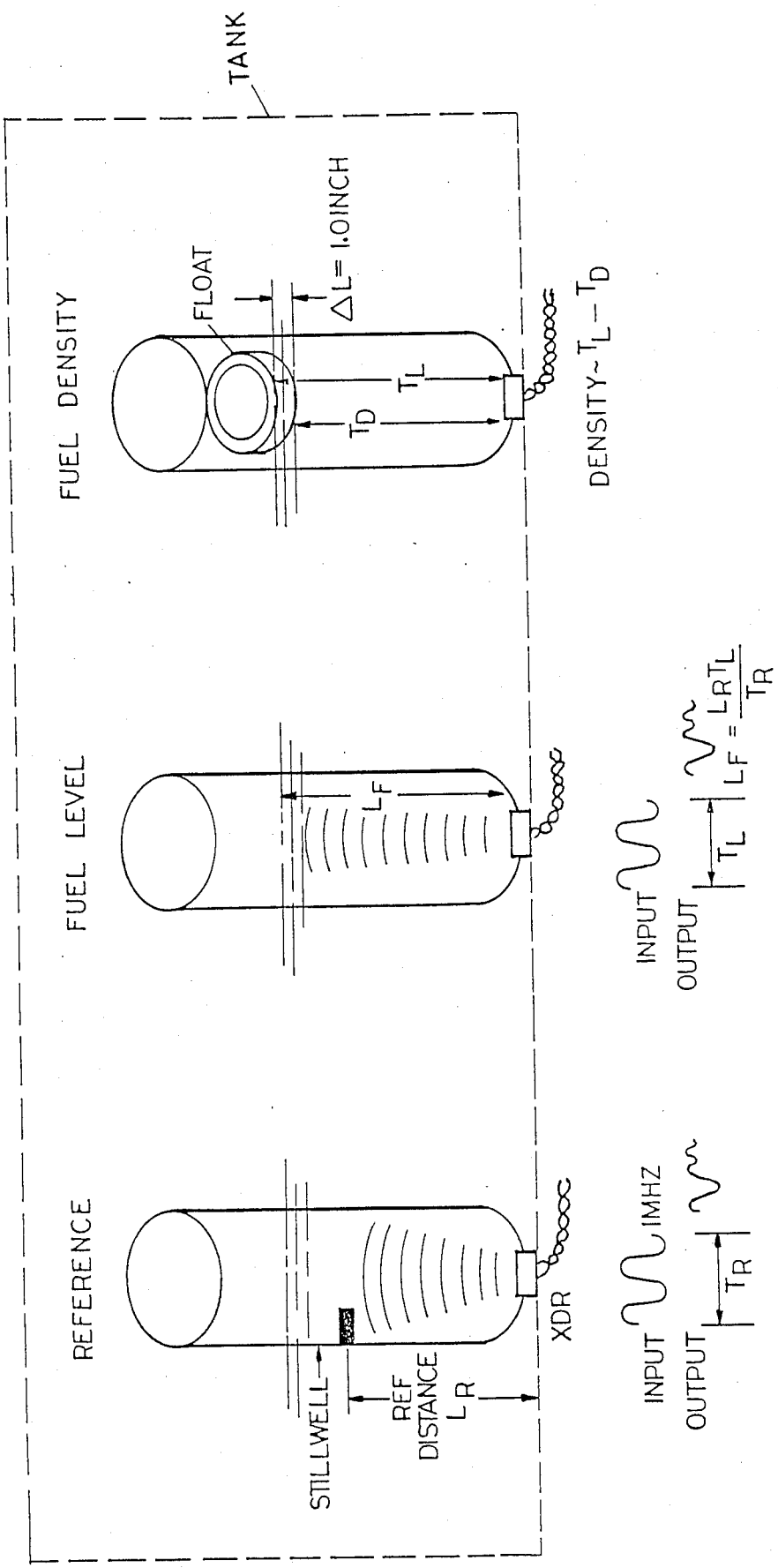
FIG. 2 is a schematic presentation of ultrasonic measurement using an ultrasonic fuel quantity gauging system in accordance with the invention.

Preferably, the ultrasonic sensor is a piezoelectric transducer with a resonant frequency of 1 MHz. The transducer is mounted at the lower end of a stillwell which has mounting flanges that are interchangeable with, and locations idential to, the existing capacitance units. Three different measurements are made within the fuel as shown in FIG. 2.

The round-trip time to the fuel surface is measured and the actual level is computed from:

$$L_F = L_R T_L \text{ where } L_F = \text{fuel level}$$
$$T_R$$

$$L_R = \text{reference distance}$$

-continued $T_L$ = round trip time to fuel surface $T_R$ = round trip time to reference reflector The fuel density is measured by determining the buoyancy of a float within the stillwell. The difference between the fuel level and the bottom of the float will vary by 1.0 inch for the variation of fuel density encountered.

$$P_F - L_F - L_D$$

$$P_F - \frac{L_R(T_L - T_D)}{T_R}$$

$P_F$ = fuel density $L_D$ = float level $T_D$ = round trip time to float bottom Fuel density is stored in non-volatile memory and corrected due to temperature changes from the reference timing measurement when the float is touching the top or bottom of the tank.

The acoustic sensor bodies are constructed of aluminum. All aluminum parts are made corrosion resistant by plating with a sulfuric anodize.

Four holes at the base of each sensor assembly allow fluid to enter the stillwell, while four holes at the top allow air to pass.

The acoustic sensing element is constructed of a piezo-ceramic material. The sensing element operates in a reciprocal mode, acting as both transmitter and receiver. The ceramic resonates at 1 MHz and possesses low Q characteristics.

The low Q characteristics manifest themselves in two ways. First, the transducer will operate over a broad frequency range and, second, the unit can detect very low fluid levels. Low fluid level detection is made possible because the element can respond to very short transmit pulse lengths and stops "ringing" very quickly at the end of the transmit pulse.

The sensing element is encapsulated in an epoxy resin. The epoxy is immersion compatible with fuels.

The sensing element contains shielding suitable for meeting both the radiated emissions and radiated susceptibility requirements.

Figure 3:
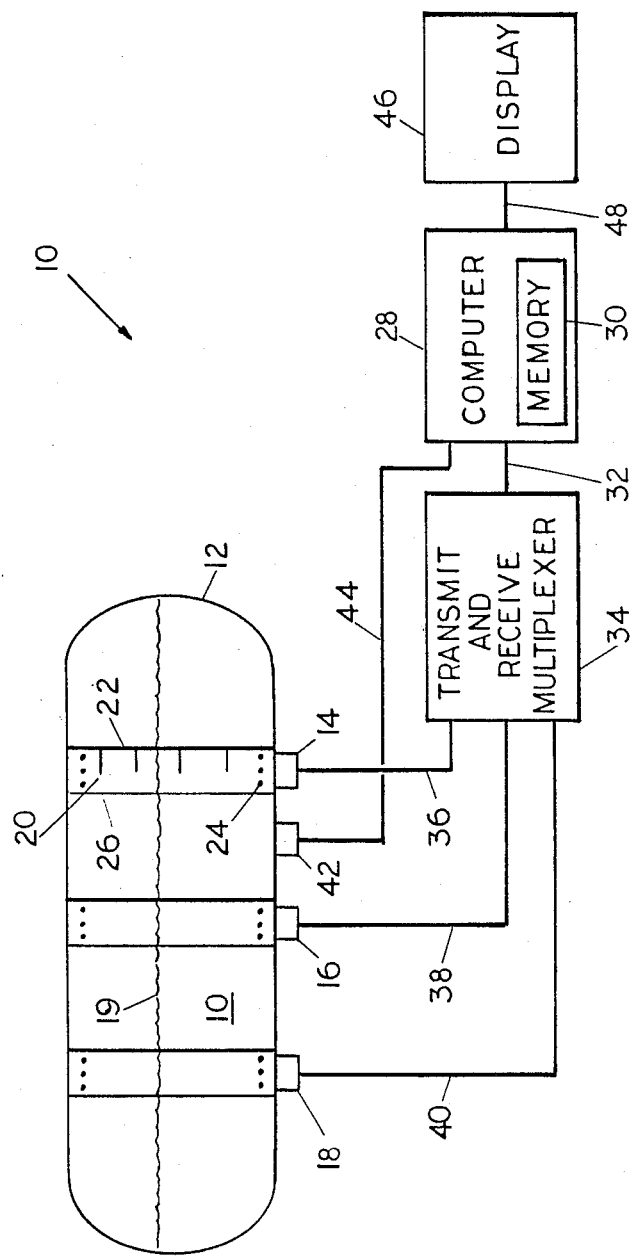
FIG. 3 is a schematic presentation of a preferred embodiment of an ultrasonic fuel quantity gauging system in accordance with the invention.

A schematic presentation of an ultrasonic fuel quantity gauging system 10 in accordance with the invention is shown in FIG. 3. Fuel 10 quantity within an aircraft tank 12 is measured using an ultrasonic transducer(s) mounted at the bottom of the tank. The transducers 14, 16 and 18 can be mounted external or internal to the tank wall. Timing measurements of the pulse-echo to the fuel surface and back and over a reference distance are combined to determine depth to the liquid surface 19 and hence volume. As shown in FIG. 3 each reference 20 extends perpendicular to the central stillwell axis. Density is inferred from the reference time measurement and fuel temperature. Fuel stratification is determined using multiple references 20 in a vertical plane. The acoustic signal is contained within a small cylindrical nonmetallic stillwell 22 with small holes 24 and 26 at the top and bottom to allow for operation at severe attitudes and fuel sloshing. The stillwell also minimizes the effects of aeration. The computer 28 is internally connected to memory 30. Computer processing is used for filtering, computations, level tracking, and interference control. Computer 30 is connected by line 32 to transmit and receive multiplexer 34. Multiplexer 34 is connected to transducers 14, 16 and 18 by lines 36, 38 and 40 respectively.

Temperature sensor 42 is preferably a thermocouple. Temperature sensor 42 is connected to computer 28 by line 44. Display 46 is connected to computer 28 by line 48.

The block diagram for a preferred ultrasonic system in accordance with the invention is shown in FIG. 3. The sensors located at the bottom of the fuel tank operate in the reciprocal or dual mode and are multiplexed under control of the computer. The quantity of sensors is determined from the tank geometry, attitude limits and required accuracy. Cylindrical tubes, referred to as stillwells, with small holes at the top and bottom are placed over each sensor to contain the acoustic signal and allow for operation at severe attitudes and under slosh conditions. The stillwells also have the beneficial effect of reducing the required sampling time and operation in aerated fuel.

Reflectors are provided in at least one stillwell for reference timing measurement. Multiple reflectors are used to measure for fuel stratification. Fuel temperature in conjunction with reference time measurement are used to infer density. Height volume tables, specific to each probe location are used to compute fuel volume. Mass is calculated knowing volume and density and displayed.

Fuel density is preferably computed from measured temperature and speed of sound based on velocity (V) and temperature (T) stored in the memory of the computer.

$$D = -2.718 + 0.0208T + 0.00682V$$

where
D = Density, Pounds per Gallon
V = Velocity of sound in a particular fuel in meters/second at a particular temperature
T = Temperature of fuel.

For specific temperatures the velocity of sound (for example in meters per second) and the density (for example in pounds per gallon) for the particular fuel in the tank 12 are measured and stored in the memory 30.

This equation was based on jet fuel samples and the one sigma error is 0.51%. Fuel density stratification is determined using multiple references in a vertical plane.

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A method of measuring aircraft fuel quantity and density comprising:
   (a) providing a fuel container means a stillwell, an ultrasonic transducer,
   a temperature sensor means,
   liquid fuel,
   a computer control means,
   indicator means,
   said computer control means comprising a central processing unit and memory means, said memory having container volume and fuel temperature data stored therein,
   said central processing unit being connected to each said ultrasonic sensor means, said central processing unit being connected to said temperature sensor means,
   said indicator means being connected to said central processing means,
   said stillwell being supported by said container means;
   said ultrasonic transducer being supported within said stillwell by said container means;
   said liquid fuel being supported within said container means;
   (b) transmitting an ultrasonic signal from said transducer within said stillwell;
   (c) receiving said ultrasonic signal by said transducer within said stillwell;
   (d) measuring the round-trip time period from said transmitting to said receiving said signal;
   (e) determining the quantity of fuel in said container means from said round-trip time period and said stored data on the container volume in said central processing unit;
   (f) determining the density of said fuel from said stored temperature data.

2. A method of measuring the mass of aircraft fuel in an aircraft fuel container, comprising:
   providing a fuel container, a stillwell,
   an ultrasonic transducer,
   a temperature sensor,
   liquid fuel,
   a computer control,
   an indicator,
   said computer control comprising a central processing unit and a memory, said memory having container volume and fuel temperature data stored therein,
   said central processing unit being connected to each said ultrasonic transducer, said central processing unit being connected to said temperature sensor,
   said indicator being connected to said central processing unit,
   said stillwell being supported by said container;
   said ultrasonic transducer being supported within a stillwell by said container means;
   said liquid fuel being supported within said container;
   transmitting an ultrasonic signal from said transducer within said stillwell;
   receiving said ultrasonic signal by said transducer within said stillwell;
   measuring the round-trip time period from said transmitting to said receiving of said signal;
   determining the velocity of sound in said fuel;
   determining the temperature of said fuel;
   determining the density of said fuel from said velocity and said temperature,
   determining in said central processing unit the volume of fuel in said container from said round-trip time period and said data on container volume stored in said memory
   determining the mass of said fuel from said fuel density and said volume of said fuel.

* * * * *

UNITED STATES PATENT AND TRADEMARK OFFICE
CERTIFICATE OF CORRECTION

PATENT NO. : 4,815,323

DATED : March 28, 1989

INVENTOR(S) : ELLINGER AND JONES

It is certified that error appears in the above-identified patent and that said Letters Patent is hereby corrected as shown below:

On the title page, item [57] Abstract, line 13, "ulrasonic" should read --ultrasonic--
line 15, "reciving" should read --receiving--

Column 1, line 51, "determing" should read -- determining--

Column 3, line 35, "attutude" should read --attitude--

Column 3, line 57, "idential" should read --identical--.

Signed and Sealed this

Twenty-sixth Day of December, 1989

*Attest:*

JEFFREY M. SAMUELS

*Attesting Officer*   *Acting Commissioner of Patents and Trademarks*